US006372230B1

(12) United States Patent
Schincaglia et al.

(10) Patent No.: US 6,372,230 B1
(45) Date of Patent: Apr. 16, 2002

(54) SKIN CARE COMPOSITION, ITS USE AND APPARATUS FOR THE APPLICATION THEREOF

(75) Inventors: Nick J. Schincaglia, Toronto; Robert Fowle, Bolton, both of (CA)

(73) Assignee: Nick Joseph Schincaglia, Toronto (CA)

( * ) Notice: Subject to any disclaimer, the term of this patent is extended or adjusted under 35 U.S.C. 154(b) by 0 days.

(21) Appl. No.: 09/299,904

(22) Filed: Apr. 28, 1999

(51) Int. Cl.[7] .............................. A61K 6/00; A61K 7/00
(52) U.S. Cl. ........................................ 424/401; 424/400
(58) Field of Search ................................ 424/400, 401, 424/402; 510/130

(56) References Cited

U.S. PATENT DOCUMENTS

| 4,617,949 | A |   | 10/1986 | Hofmann-Igi |
| 4,619,014 | A |   | 10/1986 | Piken |
| 4,854,333 | A | * | 8/1989  | Inman et al. ................ 132/209 |
| 5,648,083 | A | * | 7/1997  | Blieszner et al. ........... 424/402 |
| 5,655,257 | A |   | 8/1997  | Chavez |
| 5,776,917 | A | * | 7/1998  | Blank et al. ................ 514/519 |
| 6,156,713 | A | * | 12/2000 | Chopra et al. .............. 510/130 |

* cited by examiner

Primary Examiner—Dameron L. Jones
(74) Attorney, Agent, or Firm—Sim & McBurney

(57) ABSTRACT

The present invention is directed to a skin care composition, use of the composition, particularly on unexposed skin areas, and an apparatus for applying the composition to such unexposed and hard to reach skin areas. The composition is most suitable for application to unexposed skin to alleviate dryness, itchiness, odor and/or bacterial growth and comprises from about 0.5 to about 3.0% by weight skin-protectant agent, from about 0.5 to about 3.0% by weight preservative, from about 25 to 50% by weight alcohol, and the remainder being water.

20 Claims, 3 Drawing Sheets

SKIN CARE COMPOSITION, ITS USE AND APPARATUS FOR THE APPLICATION THEREOF

FIELD OF THE INVENTION

The present invention is directed to a skin care composition, use of the composition, particularly on unexposed skin areas, and an apparatus for applying the composition to such unexposed and hard to reach skin areas.

BACKGROUND OF THE INVENTION

When skin is covered for a prolonged period of time, itching and flaking occur. This is often accompanied by a build-up of bacteria on the skin surface leading to malodour. This often occurs, for example, on unexposed skin covered by a cast or the scalp beneath a hairpiece.

In the case of hairpieces, modern attachment methods allow for hairpieces to be worn for extended periods of time under various conditions of high winds, during recreational activities and while playing vigorous sports. Attachment is typically accomplished by sewing or weaving the hair to existing hair, by clips, by two-sided adhesive tape or by surgical methods such as suture loops or pin implants. While, these methods allow the hairpiece to fit snugly over the scalp and to be worn for extended periods of time, due to the hairpiece having a mesh, lace or polyurethane base, the scalp is not allowed to breathe resulting in the accumulation of bacteria and dead skin between the scalp and the hairpiece leading to severe itchiness, odor and even in some instances skin necrosis.

Previously, attempts have been made to use various types of scrubbing implements such as toothbrushes or backscratchers to address this problem. Still other devices have been developed for cleaning the scalp beneath a hairpiece. For example, U.S. Pat. No. 4,619,014 discloses a scalp cleaner which comprises a thin sponge-like member attached to a handle. U.S. Pat. No. 5,665,257 discloses a scalp scrubber which can be attached to a blow dryer. While these devices are useful for cleaning the scalp, they have a fairly large circumference and do not provide the leverage required to reach around the crown to the areas where the hairpiece is attached. Thus, such devices are useful only for cleaning portions of the top of the head and furthermore do not include an active composition to help alleviate and minimize the underlying problems and therefore require less cleaning of the scalp with such devices.

U.S. Pat. 4,617,949 discloses a scalp applicator which does apply liquid to the scalp, however, the applicator is not designed such that it can be used to apply a liquid to hard to reach areas beneath a hairpiece.

There is therefore a need to develop a simple and efficient method for cleaning the scalp underneath a hairpiece which overcomes the problems discussed above.

SUMMARY OF THE INVENTION

In accordance with the present invention there is provided a novel composition for the treatment of unexposed skin which is prone to itchiness, flakiness, bacterial growth and malodour. The composition is particularly useful for application to the scalp covered by a hairpiece and to skin covered for a prolonged period of time with a cast or bandage. The present invention also provides an apparatus for the application of the composition to such difficult to reach unexposed skin.

According to an object of the present invention there is provided a composition for application to unexposed skin to alleviate dryness, itchiness, odour and/or bacterial growth, said composition comprising:

from about 0.5 to about 3.0% by weight skin-protectant agent;

from about 0.5 to about 3.0% by weight preservative, from about 25 to 50% by weight alcohol, and the remainder being water.

The composition is particularly useful for treating any skin that is covered for extended periods of times and thus susceptible to bacterial growth, flakiness, itching and bad odour.

According to another object of the present invention there is provided a composition for application to unexposed skin to alleviate dryness, itchiness, odour and/or bacterial growth, said composition comprising:

from about 0.5 to about 3.0% by weight skin-protectant agent;

from about 0.5 to about 3.0% by weight preservative, from about less than 1.0% by weight thickening agent;

from about 0.5 to about 3.0% by weight anti-fungal agent;

from about 25 to 50% by weight alcohol, from about 0.05 to 3.0% by weight healing agent;

from about 0.1% to about 1.0% fragrance; and the remainder being water.

According to yet a further object of the present invention is an apparatus for the dispersal of a skin care composition to hard to reach covered skin, the apparatus comprising a reservoir containing a skin care composition, an applicator comprising an elongate arm, and an aerosol dispensing means attached to said reservoir for dispensing said composition through said applicator.

BRIEF DESCRIPTION OF THE DRAWINGS

A detailed description of the preferred embodiments are provided herein below with reference to the following drawings in which.

Figure 1:
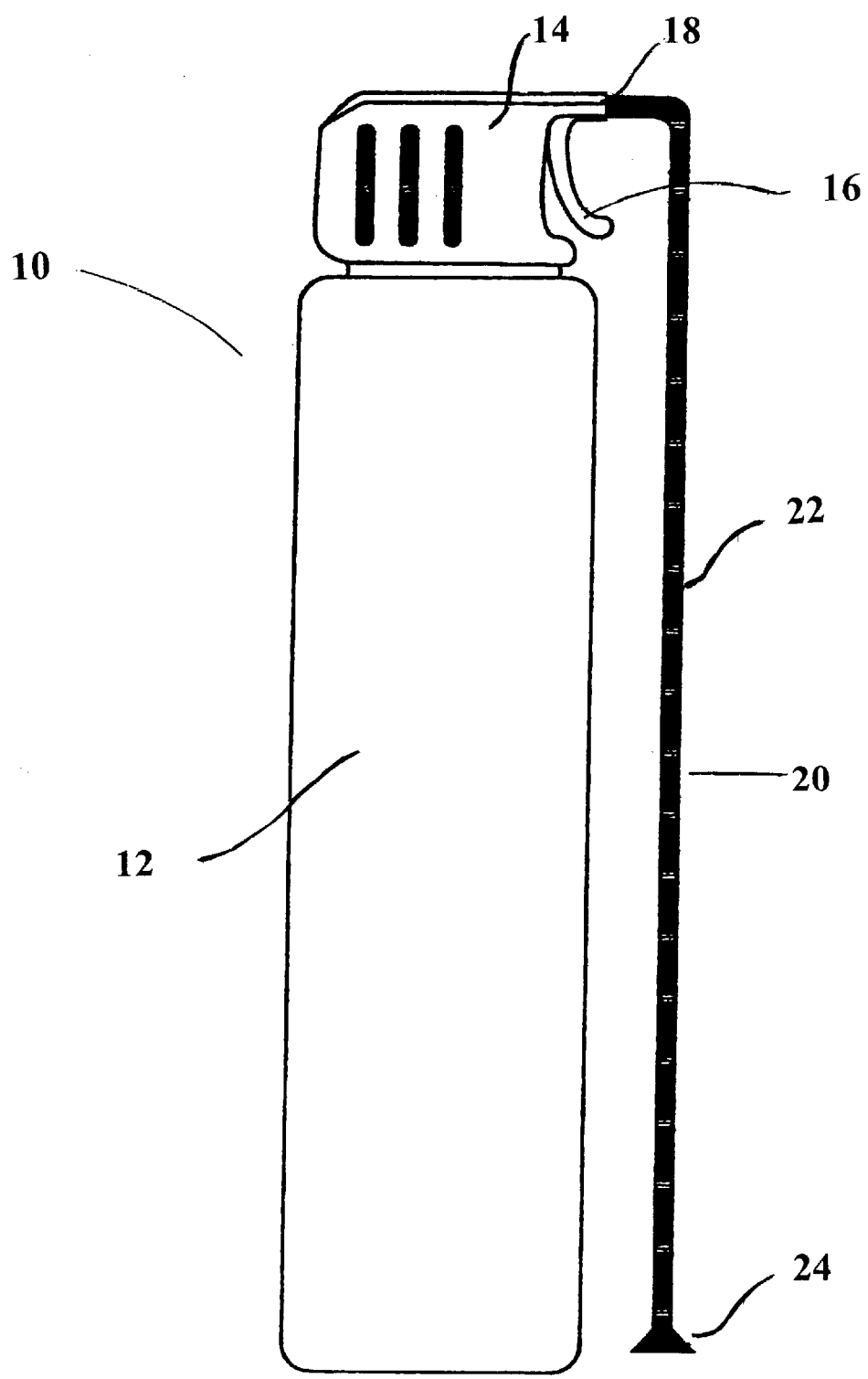
FIG. 1 is a side elevational view illustrating one embodiment of the apparatus of the present invention.
Figure 2:
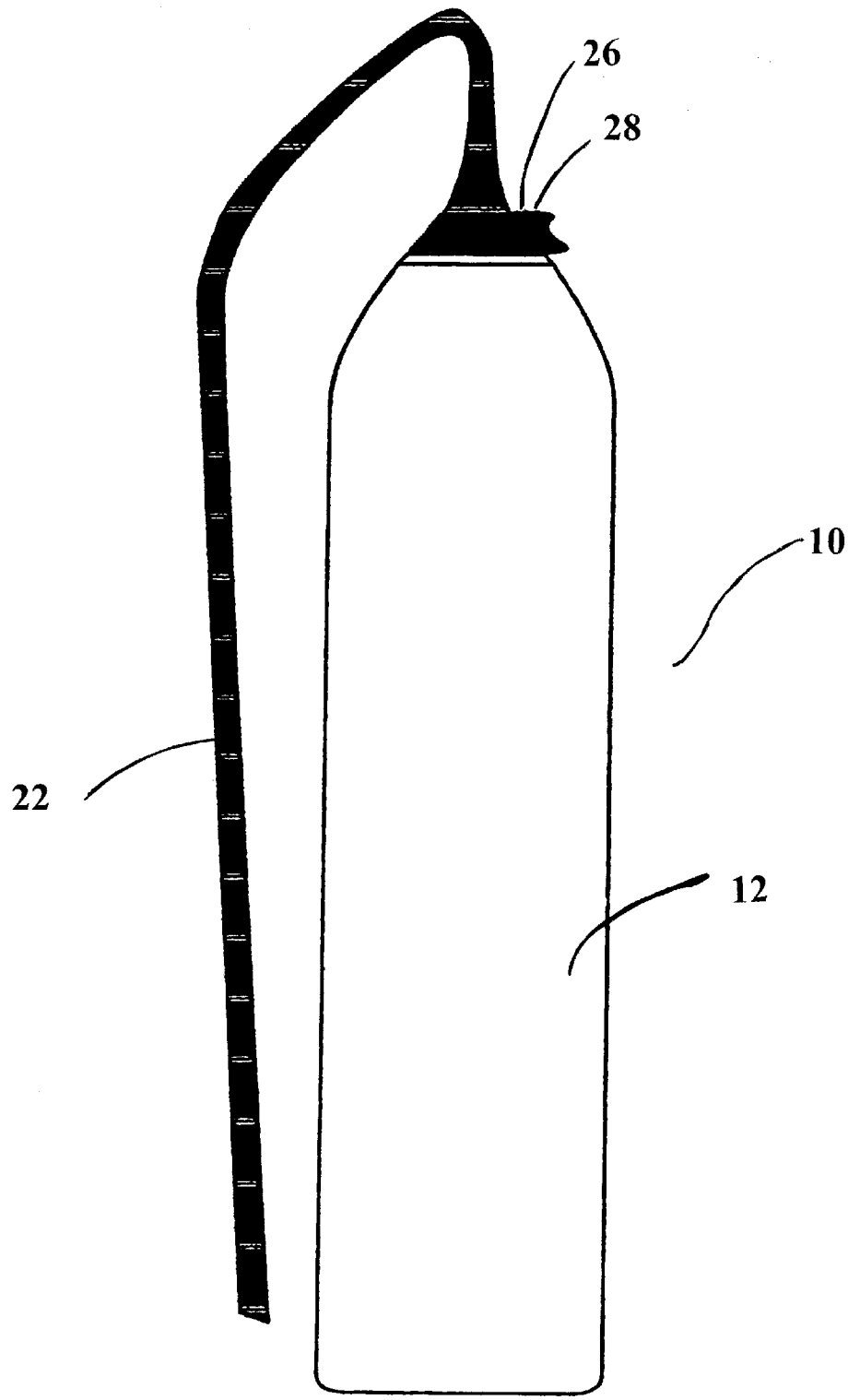
FIG. 2 is a side elevational view illustrating a farther embodiment of the apparatus of the present invention.
Figure 3:
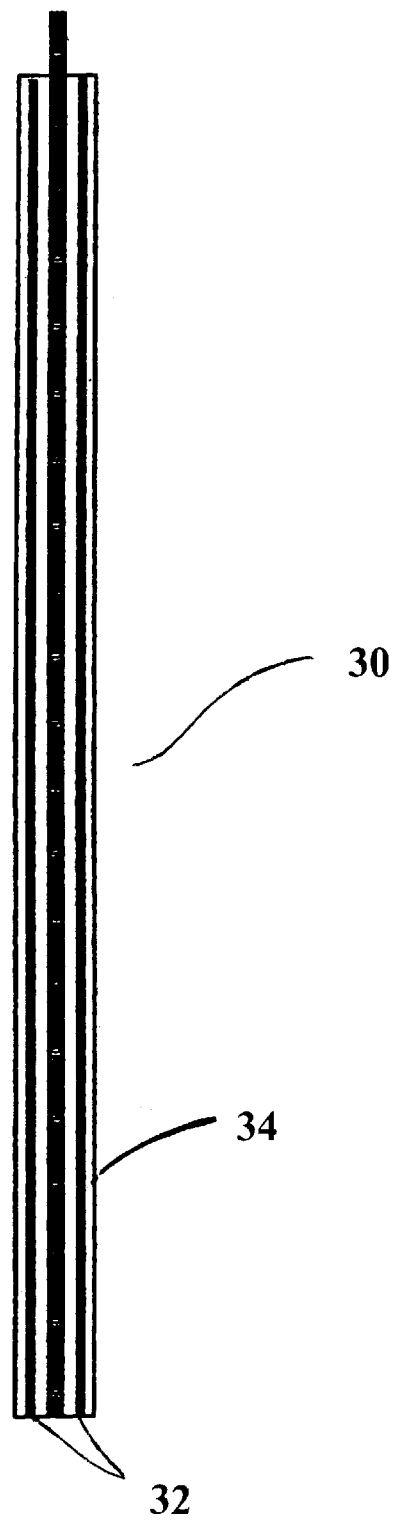
FIG. 3 is an axial sectional view of one embodiment of an extendable arm for use with the apparatus of the present invention.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENTS

The present invention is directed to a composition for treating skin that is generally covered for an exposed period of time. In particular, the invention relates to the use of the composition on long-term unexposed skin and an apparatus for dispensing the composition into hard to reach areas to access such skin. The composition comprises a skin protectant agent, a preservative and alcohol. The term skin protectant agent as used herein encompasses agents sometimes called cell proliferants, epithelization stimulants, anti-irritant agents, keratolytic agents and chemical debriders. The composition when used on a regular basis prevents the accumulation of bacteria on the skin thus minimizing skin flakiness, itchiness and odour.

A preferred skin protectant agent for use in the present composition is 5-ureidohydantoin, also known as Allantoin™. Allantoin™ is a white, odorless, crystalline powder and under basic conditions, it is anionic. While Allantoin™ has previously been incorporated into various creams and powders, it is difficult to maintain in solution. In the present invention, however, Allantoin™ is dispersed within the composition to provide an aerosol formulation which is capable of reaching into difficult areas. This is accomplished through the addition of about less than 1.0% thickening agents such as silica, methyl cellulose, hydroxy propyl cellulose and/or other suitable agents which prevent the powder from settling on the bottom of the reservoir. While reference has thus far only been made to Allantoin™ as the skin protectant agent, it is clearly apparent to those skilled in the art that other agents such as Providerm SK3™ could also be used in the composition of the present invention. The skin protectant agent typically comprises from about 0.5 to 3.0 percent by weight of the total composition. The composition may optionally include other healing agents in an amount of about 0.05% to about 3% by weight such as aloevera, zinc oxide, calamine and the like as well as about 0.1 to 1.0% by weight fragrance.

In addition to the skin protectant agent, the composition also typically includes a preservative such as Dowicil 200™. Other preservatives which may be used include, but are not restricted to, Germall 155™ (imidazolidinyl), Germall 11™ (diazolldinyl urea), Glydant™ and Glydant XL-100™ (DMDM hydantoin), Glydant Plus™ or Kathon CG™ (methylisothiazolinone) and so on. The preservative is present in about 0.5 to 3.0 percent by weight of the total composition.

An anti-fungal agent such as selenium sulphide, is optionally included in the formulations in the range of about 0.5 to 3.0% by weight. Other antibacterial agents can also be incorporated into the composition of the present invention in about 0.5 to 3.0% by weight as one skilled in art would readily recognize.

The composition also includes an alcohol component, preferably medical grade isopropyl alcohol. When the composition is applied to the skin, the alcohol dries quickly leaving a cool fresh feeling and a fresh scent. The alcohol is present in about 25 to 50% by weight of the total composition. This also promotes a medium which is unfavourable to the growth of bacteria. Water comprises the remainder of the composition.

An exemplary formulation for the composition is outlined in the table below:

| COMPONENT | % BY WEIGHT approximate %'s |
|---|---|
| Water | 60.8 |
| Isopropyl alcohol | 33 |
| Dowicil-200 ™ | 2 |
| Selenium sulphide | 2 |
| Allantoin | 2 |
| Fragrance | 0.2 |

The composition is used to protect and/or treat skin which is left unexposed to air for a period of time. It is particularly used to help prevent itchy, flaky scalp and the development of malodorous pockets beneath a hairpiece. It may also be used to soothe and relieve the itch associated with skin encased within a cast and to promote the healing of skin under bandages. The composition is also useful to treat other conditions caused by a lack or reduced air supply to the skin such as is the case with bed sores. The composition can also be applied to healthy skin to prevent the growth of bacteria leading to itchy, dry flaky skin and malodourous conditions. It may also be used to cleanse away necrotic tissue and hasten the growth of new tissue as well as to prevent the build-up of bacteria and dead skin.

The composition may be used as often as required and desired. In the case of a hairpiece, it is preferred that the composition be applied to the scalp prior to the attachment of the hairpiece. It can then be applied to the covered scalp every day, even twice a day if desired. Less frequent use may also be effective. The composition can be applied to the skin beneath a cast as required to alleviate symptoms of malodour, itchiness and flakiness of the skin. The composition is substantially non-irritating.

Similar regimens of use apply to other applications such as treatment of skin under a cast.

The composition may be formulated for topical use as a cream, lotion or liquid. Preferably, the composition is formulated in such a manner that the powders, such as the Allantoin ™, remain in suspension and all the ingredients are appropriately dispersed. The preferred form of the composition is as an aerosol spray. It is clearly apparent that, in order to be effective, the composition must be able to access hard to reach areas such as the area around the back of the head where a hairpiece is attached. The present invention renders such access attainable through a combination of the formulation of the composition and the apparatus as described below.

A preferred embodiment of the apparatus of the present invention is shown in FIG. 1. The apparatus 10 includes a canister type reservoir 12 to which a dispenser 14 is attached. In the illustrated embodiment, the dispensing means comprises a spray nozzle 14 which is activated by a trigger 16 to pump the composition through the spout 18. The applicator 20 comprises a flexible arm 22 which may be either permanently or removably attached to the spout 18. The arm 22 may range from 2 inches to 20 inches or more depending on the application. For example, a longer arm is obviously need to extend into a leg cast than to extend under a hairpiece. The arm 22 is typically constructed of a flexible plastic-type material. A dispersal funnel 24 may be optionally located at the free end of the arm.

FIG. 2 illustrates another embodiment in which the flexible arm 22 is attached to a "hair mousse type" dispenser 26 which is activated by pushing on the head 28. This configuration is particularly useful in situations where it is difficult to maintain the reservoir 12 in an upright position while dispensing. FIG. 3 illustrates an extendable dispensing arm 30 which can be used in conjunction with the flexible dispensing arm 22 to provide an overall longer arm. This is particularly useful in situations where a longer arm is needed, such as to reach inside a cast. Metal guides 32 may be included to provide for greater maneuverability over longer distances. The guides 32 and the extendable dispensing arm 30 are encased within a plastic sleeve 34.

The canister is a typical canister of plastic or metal, or it may be any other type of reservoir to which dispensing means can be attached. The dispensing means can be any typical type of dispensing means such as an aerosol spray nozzle, a spray pump attachment or a push type mechanism such as those typically found on hair mousse containers.

Upon actuation of the dispensing means, the composition is dispensed into the applicator. The applicator for use under a hairpiece is designed to have extendable arms which are able to penetrate the various means used for attachment of the hairpiece to the scalp and deliver the composition to the affected covered areas. The composition so delivered is compatible with the adhesives which may be used to adhere the hairpiece to the scalp. Typically the applicator is placed under the hairpiece via the front portion where the adhesive strip is located or, alternatively, it may be inserted around the perimeter where the hairpiece is woven to the naturally occurring hair. The applicator is small enough to easily fit into the confined area and the aerosol nature of the composition enhances dispersal. When used, for example, to reach areas covered by a cast, the applicator may be longer and can be slid down the inside of the cast.

To use the apparatus of the present invention, the arm 22 or 30 is positioned close to the area to be treated. Due to the small profile of the arm, it can easily be maneuvered within a confined area and can gain access to previously unreachable areas. The dispensing means is then actuated and the soothing and healing composition is dispersed through the applicator to the affected area. The surface area that can be treated is enhanced due to the dispersion properties of the composition, i.e. it is an aerosol formulation. Thus the composition, when applied using the apparatus, cleanses away necrotic tissue and promotes the growth of healthy tissue in hard to reach places and addresses the problems of itch and disagreeable odors previously associated with skin that remains covered for prolonged periods.

It is appreciated that the apparatus of the present invention while ideal for use with the composition of the present invention, it can be used to apply various types of compositions as desired to hard to reach skin that is unexposed or simply hard to reach.

In summary, the present invention provides a composition and an apparatus for use with the composition to help alleviate bacterial growth, malodour, itching and flaking of skin which is left unexposed to the air for long periods of time. Such conditions are typically present with hairpieces, casts and bandages. The apparatus helps to facilitate the dispersal of the composition to hard to reach areas such as those under a hairpiece and beneath a cast for example. The composition and apparatus are easy to use and effective.

Although preferred embodiments have been described herein in detail, it will be clear to one skilled in the art that variations may be made thereto without departing from the nature of the invention or the scope of the appended claims.

We claim:

1. A composition for application to unexposed skin to alleviate dryness, itchiness, odour and/or bacterial growth, said composition comprising:
   i) from about 0.5 to about 3.0% by weight skin-protectant agent selected from the group consisting of Allantoin and Providerm SK3™;
   ii) from about 0.5 to about 3.0% by weight preservative;
   iii) from about 25 to about 50% by weight alcohol;
   iv) from about 0.5 to about 3.0% by weight selenium sulphide; and
   v) the remainder being water.

2. The composition of claim 1, wherein said composition further comprises from less than about 1.0% by weight of a thickening agent.

3. The composition of claim 2, wherein said thickening agent is selected from the group consisting of silica, methyl cellulose and hydroxypropyl cellulose.

4. The composition of claim 1, wherein said composition further comprises about 0.05 to 3.0% by weight healing agent.

5. The composition of claim 4, wherein said healing agent is selected from the group consisting of aloevera, zinc oxide and calamine.

6. The composition of claim 1, wherein said composition further comprises about 0.1 to 1.0% by weight fragrance.

7. The composition of claim 1, wherein said composition further comprises about 0.5 to 3.0% by weight of an antifungal agent.

8. The composition of claim 1, wherein said composition farther comprises an antibacterial agent.

9. The composition of claim 1, wherein said preservative is selected from the group consisting of Dowicil™, Germall 155™, Germall 11™, Glydant™, Glydant XL-100™, Glydant Plus™ and Kathon CG™.

10. The composition of claim 1, wherein said alcohol is isopropyl alcohol.

11. The composition of claim 1, wherein said composition is provided as a liquid, cream or lotion.

12. The composition of claim 11, wherein said composition is provided as an aerosol liquid.

13. A composition for application to unexposed skin to alleviate dryness, itchiness, odour and/or bacterial growth, said composition comprising:
   i) from about 0.5 to about 3.0% by weight skin-protectant agent selected from the group consisting of Allantoin and Providerm™;
   ii) from about 0.5 to about 3.0% by weight preservative,
   iii) from about less than 1.0% by weight thickening agent;
   iv) from about 0.5 to about 3.0% by weight selenium sulphide;
   v) from about 25 to 50% by weight alcohol,
   vi) from about 0.05 to 3.0% by weight healing agent;
   vii) from about 0.1% to about 1.0% fragrance; and
   viii) the remainder being water.

14. The composition of claim 13, wherein said composition further comprises an antibacterial agent.

15. A method of treating covered skin; said method comprising applying a therapeutically effective amount of the composition of claim 1 to said covered skin.

16. A method of treating skin under a hairpiece; said method comprising applying a therapeutically effective amount of the composition of claim 1 to said skin under a hairpiece.

17. A method of treating skin covered by a cast; said method comprising applying a therapeutically effective amount of the composition of claim 1 to said skin.

18. A method of treating bedsores; said method comprising applying a therapeutically effective amount of the composition of claim 1 to said bedsores.

19. A composition for application to unexposed skin to alleviate dryness, itchiness, odour and/or bacterial growth, said composition comprising:
   i) from about 0.5 to about 3% by weight skin-protectant agent selected from the group consisting of Allantoin and Providerm™;
   ii) from about 0.5 to about 3% by weight Dowicil 200™;
   iii) from about 25 to about 50% by weight alcohol;
   iv) from about 0.5 to about 3% by weight of selenium sulphide; and
   v) the remainder being water.

20. A composition for application to unexposed skin to alleviate dryness, itchiness, odour and/or bacterial growth, said composition consisting of:
   i) from about 0.5 to about 3.0% by weight skin-protectant agent selected from the group consisting of Allantoin and Providerm™;
   ii) from about 0.5 to about 3.0% by weight preservative,
   iii) from about 0.05 to about 3.0% by weight aloe vera;
   iv) from about 25 to 50% by weight alcohol;
   v) from about 0.5 to about 3% by weight of selenium sulphide; and
   vi) the remainder being water.

* * * * *